United States Patent [19]

Morrow

[11] 4,447,912
[45] May 15, 1984

[54] CRIPPLED HAND ASSISTING DEVICE

[75] Inventor: Rosemary K. Morrow, Huntington Beach, Calif.

[73] Assignee: Philip A. Putman, Huntington Beach, Calif.

[21] Appl. No.: 466,225

[22] Filed: Feb. 14, 1983

[51] Int. Cl.³ .................. A61F 5/10; A41D 19/00
[52] U.S. Cl. ............................. 2/159; 2/160; 2/DIG. 6; 128/77
[58] Field of Search ............... 2/16, 20, 159, 161 R, 2/161 A, DIG. 6, 160; 128/77

[56] References Cited

U.S. PATENT DOCUMENTS

| | | | |
|---|---|---|---|
| 3,348,238 | 10/1966 | Hydock | 2/161 A |
| 3,368,811 | 2/1968 | Finney | 2/159 R |
| 3,408,657 | 11/1968 | Gallagher | 2/159 |
| 3,421,160 | 1/1969 | Domenico | 2/159 |
| 3,508,280 | 4/1970 | Osborn | 2/159 |
| 3,512,776 | 5/1970 | Thomas | 2/161 A |
| 3,532,344 | 10/1970 | Masstab | 2/159 X |
| 3,547,112 | 12/1970 | Courtney | 2/159 X |
| 3,606,319 | 9/1971 | Borden | 2/161 A |
| 3,779,550 | 12/1973 | Benoun et al. | 2/161 A |
| 3,790,168 | 2/1974 | Hashimoto | 2/161 A |
| 4,051,572 | 10/1977 | Greenwood | 2/159 |
| 4,273,130 | 6/1981 | Simpson | 2/DIG. 6 |

Primary Examiner—Louis Rimrodt

[57] ABSTRACT

A prosthetic device to enable persons incapable of proper control of their fingers to manipulate objects such as brushes, pencils, or toys. It resembles a partial glove, covering only the palm, held in place with straps around the back of the hand. It uses hook and loop pile (Velcro for example) both to fasten the straps to the body and as a patch on the palm side to which objects fitted with mating pile can be attached. One strap is long enough to provide added support by passing over the handle of the object. A separate patch with a ring in the center is described—this works better for grasping reasonably rigid, extensive objects like balls.

8 Claims, 6 Drawing Figures

CRIPPLED HAND ASSISTING DEVICE

BACKGROUND OF THE INVENTION

1. Field of the Invention

The invention is in the field of prosthetic-like devices to aid persons with temporary or permanent difficulty operating their hand to grasp and use implements or toys.

2. Description of Prior Art

To applicants knowledge there exists no similar device. In hospitals often a patient is unable to grasp or unable to long retain a grasp on silverware, hair or tooth brushes, or toys because of weakness or poor control of his finger muscles. The prior art is to secure an object to the hand with a bandage or with adhesive tape. The use of bandage, though obvious, is not very efficient of the nurses time, nor does it hold the object very well unless the bandage is elaborately fastened. The use of adhesive tape has the drawback that patients of this sort usually have very tender, soft, and somewhat sensitive hands. In both expedients the nurse or other attendant must apply and remove the fastening.

As to the novelty of the structure relative to the prior art, the use of hook-and-loop pile to attach specific sporting equipment to a healthy hand is mentioned in Borden, U.S. Pat. No. 3,606,319 and Osborn, U.S. Pat. No. 3,508,280. The present invention distinguishes from these in that no cooperation of the fingers is required, and in that a separate strap not present in Borden or Osborn supplies the function of the inactive fingers. Moreover, the pesent invention represents an improvement in that finger stalls are eliminated, an advantage during application and removal.

Another advantage deriving from the absence of finger stalls is that the invention is free of restriction as to size of the hand, i.e. size of fingers and distance between the fingers. The wraparound method of attachment makes a single size capable of attachment to a wide variety of hands, unlike a full glove which must be at least roughly sized to the hand. This is a particular advantage in two respects: the attendants time is saved and the feasibility of a patient using the device can be learned using a standard size.

SUMMARY OF THE INVENTION

The invention is a partial glove, covering only the palm face of the hand. It is held in place by attached straps which pass over the back of the hand on both sides of the thumb. At least one of these straps is longer than would be required to merely fasten the glove; this strap can pass over an object such as a handle so as to press it into the hand. The straps fasten to the palm portion wherever they fit most appropriately because the surface of the palm portion is one component of hook-and-loop pile, and the strap surface is the other component. A generally rectangular patch of coarser and stronger hook-or-loop pile is fastened to the palm to provide an anchor point for the handle, which would normally be fitted with the mating pile. Since this product (hook and loop pile) has high resistance to shearing or sliding forces when the hooks are engaged with the loops, and since the strap tends to prevent separation of the components by a direct pull, the handle or object is quite firmly attached to the hand. This is obviously necessary to make the device useful. This firm attachment is the primary advantage of the invention.

A second advantage over previous methods is that the invention can be quickly and easily applied to or removed from the hand. Although an attending person is desirable, much of the time the patient can do the attaching or detaching without assistance through using his other hand or his teeth or both. This feature is a benefit in a hospital environment when attendants time and attention are not always available.

A third advantage is that the bulk of contact with the hand consists of material which is soft and pliable. Moreover, since it is open to the air perspiration is not a problem, as it would be with a full glove.

DESCRIPTION OF THE PREFERRED EMBODIMENT

Figure 1:
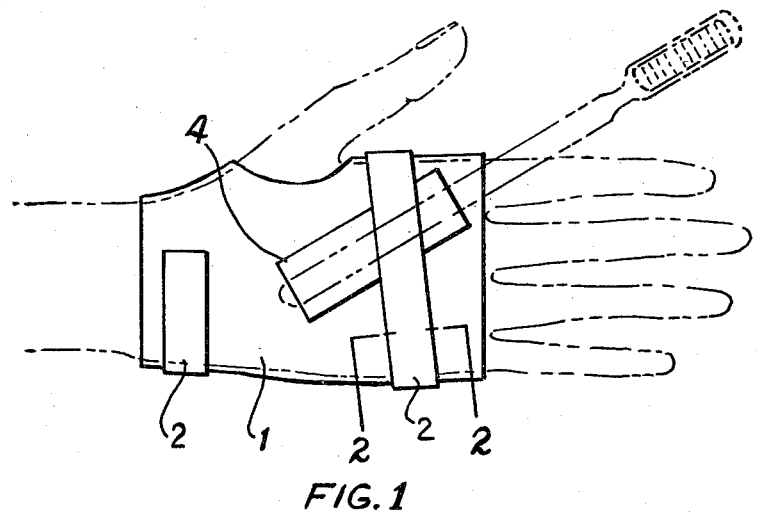
FIG. 1 is a view from the palm side of a hand on which the device has been mounted.
Figure 2:
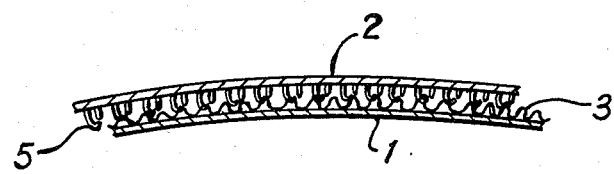
FIG. 2 is a cross-section along the line 2—2 in FIG. 1, showing the first securing means and the second securing means engaged.

The novelty of this invention being in the concept of fastening a patch of coarse and strong hook or loop pile to the hand, and at the same time providing a holding strap, it is by its nature capable of numerous embodiments. Therefore the use will be described briefly to make apparent the versatility of the device. This versatility is an important feature which is common to numerous embodiments.

In use, the body portion 1 is placed on the open hand with the elongated patch 4 exposed. The thumb is placed in cutout 6. Straps 2, which are permanently fixed to body portion 1, are passed around the back of the hand and the hooks 5 on the straps 2 are engaged with the loops 3 which cover the surface of body portion 1. Securing means other than hook and loop pile may be used equally well, but hook and loop pile is preferred. A handle object such as a toothbursh, its handle fitted with hook-and-loop pile as designed to mate with the hook-and-loop pile of patch 4, is placed in the hand before the longer of straps 2 is fully secured, and that strap is passed over the handle before both sides of it are pressed against body portion 1 the better to engage the first securing means 3, shown as loops, with the second securing means 5, shown as hooks.

The normal use having been described, it is clear that many objects may be attached to the hand by this invention. Fitting the object with pile is not essential; doing so merely improves the user's control in manipulating the object. Objects need not have handles to be attached by this invention.

Figure 5:
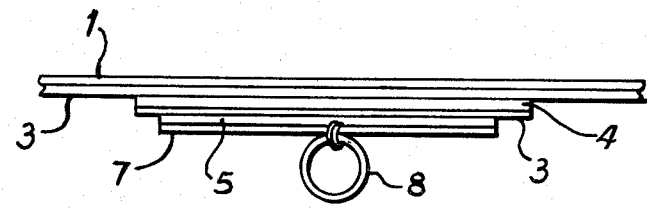
FIG. 5 is a cross-section showing the detail of a removable appendage enhancing the usefulness of the basic invention.
Figure 6:
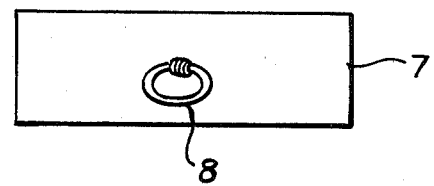
FIG. 6 is a plan view of the appendage shown in FIG. 5.

Some objects, such as balls, have been found to form only a weak attachment to patch 4. This is because hook-and-loop pile resists sliding or shearing motion, but is readily disengaged by pulling or normal forces. Therefore an integral part of this invention is the appendage shown in FIGS. 5 and 6. An eye fastener, such as a hook or ring 8, is fixed centrally to a base portion 7. Fixing may be by sewing, using adhesives, or through perforated holes in the base portion. The ball or other firm extensive object is then fitted with a mating hook fastener which, when it engages the eye, tends to concentrate any separating force at the attachment point of eye fastener 8. Thus, though the portion of hook/loop pile directly under the fastening point may disengage, portions farther away from the fastening point are inclined to slide or shear. This sliding or shearing is prevented because the pile resists such motion. Therefore it has been found that a higher separating force is required when the force is applied at the midpoint of a patch rather than at an edge. The appendage shown in FIGS. 5 and 6 uses this finding, and when the appendage is used the patient has much firmer control of relatively firm objects larger than the patch 4.

Figure 3:
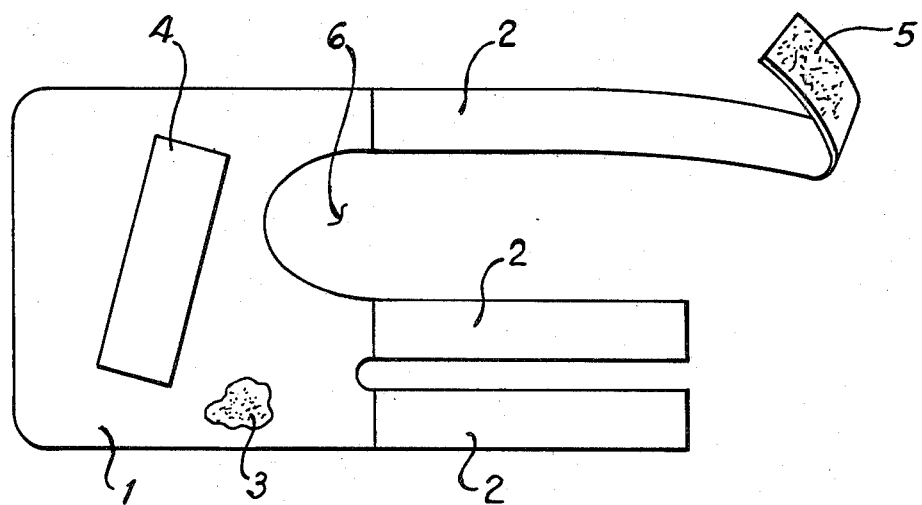
FIG. 3 is a semi-plan view of the palm side of a right-handed version of the device.

FIG. 3 shows the preferred embodiment. When the exception of the placement of elongated patch 4 this figure has been fully described by the above discussion. Patch 4 is placed diagonally on the surface of body portion 1, closer to the point of attachment of the third and longer strap 2 and farther from the attachment point of the other straps 2. This permits the handles of objects to be directed sideways from the hand, protruding between the idex finger and the thumb. If the user/patient has any finger control at all this is the natural position for grasping.

Figure 4:
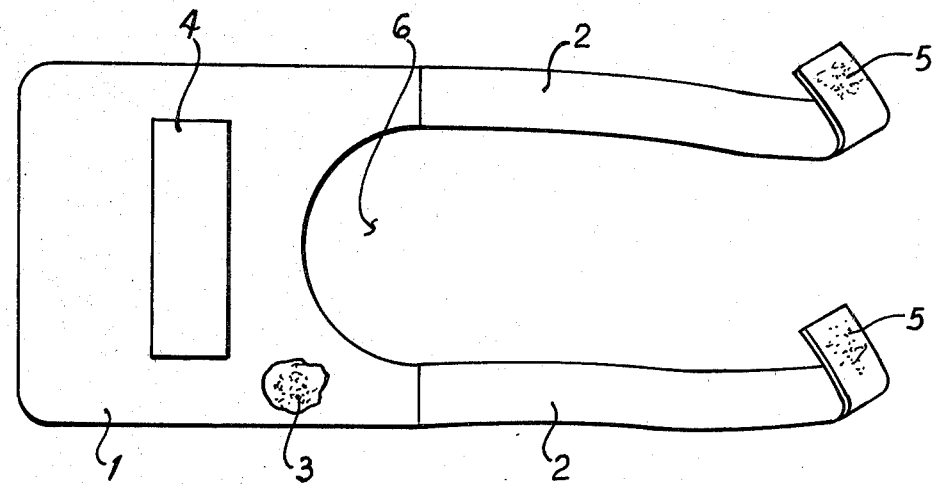
FIG. 4 is a semi-plan view of a universal version suitable for either right or left hand, as viewed from the palm side.

FIG. 1 is an alternate embodiment having one wrist strap. It is for the left hand, as determined both by the position of the longer strap and the diagonal placement of elongated patch 4. FIG. 4 is a universal embodiment usable on either right or left hand. The thumb cutout 6 is symmetrical to the body portion 1, and elongated patch 4 is also symmetrically placed.

The invention uses commercially available securing means, distinguishing between first securing means and second securing means. These two will attach to each other when pressed together, but form no force-resisting attachment when pressed against other surfaces. The only combination known to the inventor which has these properties is hook-and-loop pile, but it is obvious that any other pair of fastening means possessing the ability to resist shear force when pressed together, and to form no attachment to the other surfaces, would work in the same manner.

In all the embodiments body portion 1 is as shown. It has a roughly quadrilateral outline in the plan view. Along the side to which the straps 2 are attached there may be protrusions, one for each strap, to extend the softer body portion material along the strap a short distance. This is to minimize contact of hooks 5 or loops 3, whichever may be on the strap, with the hand particularly at the bend in the strap where fretting contact may occur during use. The thumb cutout 6 causes the body portion 1 to fit flatter in, and more securely on, the hand through skirting the mound of flesh at the base of the thumb.

The invention having been described in its preferred embodiment, it is clear that numerous variations to fit specific circumstances can be made without excerise of the inventive faculty. For example the size, position and shape of elongated patch 4 is susceptible to variation so as better to accommodate specific objects or the hands of specific patients.

I claim:

1. Apparatus to enable persons to fix objects to their hand without requiring participation of their fingers, comprising
   a body portion constructed of fabric having a roughly quadrilateral outline with a plurality of spaced protrusions along one side, and
   first securing means located on one (the outer) surface of said body portion, and
   a plurality of straps attached one to each spaced protrusion of said body portion extending in the same direction as the protrusion, and,
   second securing means located on one (the inner) surface of each said strap, said second securing means being capable of attachment to said first securing means, and
   a patch of material having on its surface a coarser version of said first securing means, fixed to the same surface of said body portion as is said first securing means,
   whereby said body portion may be placed with its inner surface against the palm of a persons open hand, then said straps may be passed around the back of the hand and across said body portion, so that through action of said first and second securing means the apparatus will be fixed to the hand with said patch of material both exposed and attached to the persons hand such that objects may be fixed thereon without requiring participation of the fingers.

2. Apparatus as described in claim 1 in which said first securing means is hook pile and said second securing means is loop pile.

3. Apparatus as described in claim 1 in which said first securing means is loop pile and said second securing means is hook pile.

4. Apparatus as set forth in claim 1 wherein said object, or handle of said object, is provided with securing means capable of being retained by said coarser patch of material fixed to the same surface of said body portion as said first securing means.

5. Apparatus as set forth in claim 1 wherein said body portion and its spaced protrusions are such that said body portion can be applied for use on either right or left hands.

6. A prosthetic-like device attaching to the hand permitting objects such as toothbrush, hair brush, or pencil to be attached thereto obviating the need to grasp the objects with the fingers, comprising
   a body portion of fabric having loop pile on one surface, sized to cover the hand from base of fingers to beyond the wrist joint, and
   three straps having hook pile on one surface, all attached to one side of said body portion with the pile surfaces of said body portion and said straps facing in opposite directions, two of said straps being of a length sufficient to overlap the body portion after being wrapped, around the wrist, the third strap being of greater length—sufficient to wrap completely around hand at the knuckles while at the same time passing over the handle of an object such as a hairbrush, toothbrush, or pencil, and
   an elongated patch of fabric having on one surface a loop pile coarser than that of said body portion, said patch being fixed to the loop pile surface of said body portion diagonally such that said patch is closer to the side of said body portion near the point of attachment of said third strap and reaches a location farther from the same side of said body portion as it extends in its elongated dimension toward the points at which said other two straps are attached, whereby said body portion may be affixed to the palm of the hand, loop pile exposed, through encircling hand and wrist with said straps followed by engaging the hook pile of said straps with the loop pile of said body portion, the hook pile of said third strap similarly encircling the hand and being attached to the loop pile of said body portion, except said third strap, passing over the object to be grasped, presses the object against said elongated patch to enhance the object-to-hand attachment.

7. A prosthetic-like device attaching to the hand permitting handles of objects such as toothbrushes, hairbrushes, or pencils to be attached thereto obviating the need to grasp the objects with the fingers, comprising

- a body portion of fabric having loop pile on one surface, sized to cover the hand from base of the fingers to beyond the thumb, and
- two straps having hook pile on one surface attached transversely to said body portion, one at the base of the fingers and one on the wrist side of the thumb, such that the loop pile of said body portion and the hook pile of said strap portion face in opposite directions, said straps being long enough to wrap completely around the hand, overlapping the hook pile of said body portion on both sides of a handle, and
- an elongated patch of fabric having on one surface a hook pile coarser than that of said body portion, said patch being fixed to the loop pile surface of said body portion with the long dimension perpendicular to said straps and extending substantially the full length of said body portion, whereby said body portion may be affixed to the palm of the hand, loop pile exposed, though encircling hand and wrist with the two straps and engaging the hook pile of said straps with the loop pile of said body portion while entrapping the handle of an object under a strap, thereby attaching the handle to the hand.

8. A device for attaching an eye fastener to a surface consisting of loop pile so as to withstand separating force, comprising

- a base portion of flexible sheet material having hook pile on one surface, and
- fastening means attaching the eye fastener at the midpoint of the other surface of said base portion, in which said base portion may be pressed throughout its full area against the surface before separating force is applied to the eye fastener hence establishing full engagement of hooks and loops, so that the pulling apart of the hook and loop pile is confined to a small region near the midpoint of said body portion and the hooks on other portions of said body portion remain engaged and capable of resisting the separating force.

* * * * *